United States Patent [19]

Butler

[11] Patent Number: 4,617,310

[45] Date of Patent: Oct. 14, 1986

[54] 5-OXO-2-PYRROLIDINEPROPANOIC ACID DERIVATIVES AND USE AS COGNITION ACTIVATORS

[75] Inventor: Donald E. Butler, Ann Arbor, Mich.

[73] Assignee: Warner-Lambert Company, Morris Plains, N.J.

[21] Appl. No.: 765,749

[22] Filed: Aug. 15, 1985

Related U.S. Application Data

[60] Division of Ser. No. 476,524, Mar. 24, 1983, Pat. No. 4,559,358, which is a continuation-in-part of Ser. No. 381,662, May 24, 1982, abandoned.

[51] Int. Cl.$^4$ .................. C07D 401/06; C07D 207/12; A61K 31/40; A61K 31/44; A61K 31/445
[52] U.S. Cl. .................................. 514/343; 514/424; 546/281; 548/543
[58] Field of Search ................ 546/281; 514/343, 424; 548/543

[56] References Cited

U.S. PATENT DOCUMENTS

| | | | |
|---|---|---|---|
| 4,064,264 | 12/1977 | Nelson | 546/281 |
| 4,324,787 | 4/1982 | Boltze et al. | 514/343 |
| 4,332,945 | 6/1982 | Edwards | 546/281 |

*Primary Examiner*—Richard L. Raymond
*Assistant Examiner*—D. Springer
*Attorney, Agent, or Firm*—Jerry F. Janssen

[57] ABSTRACT

5-Oxo-2-pyrrolidinepropanoic acids, base addition salts, esters and amides are useful as agents for the reversal of amnesia. Pharmaceutical compositions containing said compounds and methods for using said compositions for treating senility and reversal of amnesia are also taught.

6 Claims, No Drawings

5-OXO-2-PYRROLIDINEPROPANOIC ACID DERIVATIVES AND USE AS COGNITION ACTIVATORS

CROSS REFERENCE TO RELATED APPLICATION

This application is a divisional of application Ser. No. 476,524, filed Mar. 24, 1983, now U.S. Pat. No. 4,559,358 issued Dec. 17, 1985 which in turn is a continuation-in-part of application Ser. No. 381,662 filed May 24, 1982, now abandoned.

BACKGROUND OF THE INVENTION

The synthesis of 5-oxo-2-pyrrolidinepropanoic acid then known as pyrrolidin-2-one-5-propanoic acid is reported in Chem. Ber., 88, 509 (1955). The synthesis of pyrrolidin-2-one-5-propanoic acid methyl ester is reported in J. Am. Chem. Soc., 69, 690 (1947). The synthesis of pyrrolidin-2-one-5-propanoic acid ethyl ester is reported in Coll. Czech. Chem. Comm., 12, 278 (1947). Pyrrolidin-2-one-5-propanoic acid amide is reported in Chem. Ber., 55B, 3950–3960 (1922) and the piperidide of pyrrolidin-2-one-5-propanoic acid is reported in Ann., 581, 225–237 (1953). The compounds are utilized in the references as chemical intermediates or as crystalline derivatives.

SUMMARY OF THE INVENTION

The invention sought to be patented in its generic chemical compound aspect is a compound having the structural formula I

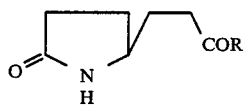

wherein R is O— as a salt with a pharmaceutically acceptable metal or amine cation;

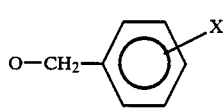

wherein X is hydrogen, alkyl of from one to six carbon atoms, alkoxy of from one to six carbon atoms, halo or trifluoromethyl; O-alkyl having 3, 4, 5, or 6 carbon atoms; or $NR_1R_2$ wherein $R_1$ is alkyl of from one to six carbon atoms or alkyl of from two to six carbon atoms substituted by amino, alkylamino, or dialkylamino in which alkyl contains one to six carbon atoms, hydroxy, or alkoxy of from one to six carbon atoms, mercapto, or alkylmercapto of from one to six carbon atoms; 5- or 6-membered cycloalkyl; 5- or 6-membered cycloalkyl substituted by alkyl of from one to four carbon atoms, phenyl, or phenyl substituted by alkyl of from one to four carbon atoms, or a 5- or 6-membered heterocyclic group containing up to four heteroatoms consisting of nitrogen, oxygen, and sulfur which may be substituted by amino, alkylamino, dialkylamino, or alkyl of from one to four carbon atoms; $R_2$ is hydrogen or alkyl of from one to six carbon atoms, or where $R_1R_2$ combine with N to form 2,6-dimethylpiperidine.

In a second generic aspect, the invention sought is a compound having the structural formula I, wherein R is O— as a salt with a pharmaceutically acceptable metal or amine cation;

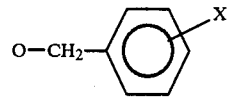

wherein X is hydrogen, alkyl of from one to six carbon atoms, alkoxy of from one to six carbon atoms, halo, or trifluoromethyl; or O-alkyl having 3, 4, 5, or 6 carbon atoms; or $NR_1R_2$ wherein $R_2$ is hydrogen, and $R_1$ is alkyl of from one to six carbon atoms, or alkyl of from two to six carbon atoms substituted by amino, alkylamino, or dialkylamino in which alkyl contains one to six carbon atoms; 2,6-dimethylphenyl, 4-amino-3-pyridinyl, 3-amino-4-pyridinyl, 4-pyridinyl, or 5-tetrazol-yl; or where $R_1R_2$ combine with N to form 2,6-dimethylpiperidine.

The invention sought to be patented in its first specific chemical compound aspect are the compounds having the names:

5-oxo-2-pyrrolidinepropanoic acid benzyl ester;
5-oxo-2-pyrrolidinepropanoic acid N-benzyl amide;
5-oxo-2-pyrrolidinepropanoic acid N-N',N'-diisopropylaminoethyl amide;
5-oxo-2-pyrrolidinepropanoic acid N-(L)α-methylbenzyl amide;
5-oxo-2-pyrrolidinepropanoic acid N-4-(aminopyridinyl)amide;
5-oxo-2-pyrrolidinepropanoic acid N-(2,6-dimethylphenyl)amide;
5-oxo-2-pyrrolidinepropanoic acid 4-(3-aminopyridinyl)amide, and
5-oxo-2-pyrrolidinepropanoic acid 3-(4-aminopyridinyl)amide.

The invention sought to be patented in its pharmaceutical composition aspect is a composition which comprises a compound having the structural formula II

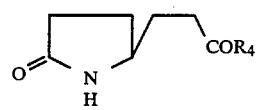

wherein $R_4$ is OH; O— as a salt with a pharmaceutically acceptable metal or amine cation;

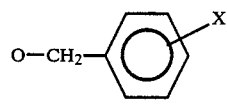

wherein X is hydrogen, alkyl of from one to six carbon atoms, alkoxy of from one to six carbon atoms, halo or trifluoromethyl; —O—alkyl having from one to six carbon atoms, or $NR_1'R_2$ wherein $R_1'$ is hydrogen, alkyl of from one to six carbon atoms or alkyl of from two to six carbon atoms substituted by amino, alkylamino, or dialkylamino in which alkyl contains one to six carbon atoms, hydroxy or alkoxy of from one to six carbon atoms, mercapto or alkylmercapto of from one to six carbon atoms; 5- or 6-membered cycloalkyl, 5- or 6-membered cycloalkyl substituted by alkyl of from one to four carbon atoms; phenyl or phenyl substituted by alkyl of from one to four carbon atoms or a 5- or 6-membered heterocyclic group containing up to four heteroatoms consisting of nitrogen, oxygen and sulfur which may be substituted by amino, alkylamino, dialkylamino, or alkyl of from one to four carbon atoms; $R_2$ is hydrogen or alkyl of from one to six carbon atoms, or where $R_1'R_2$ combine with N to form 2,6-dimethylpiperidine in combination with a pharmaceutically acceptable carrier.

The invention sought to be patented in its first specific pharmaceutical composition aspect is a compound which comprises 5-oxo-2-pyrrolidinepropanoic acid, in combination with a pharmaceutically acceptable carrier.

The invention sought to be patented in a second specific pharmaceutical composition aspect is a composition which comprises 5-oxo-2-pyrrolidinepropanoic acid ethyl ester in combination with a pharmaceutically acceptable carrier.

The invention sought to be patented in a third specific pharmaceutical composition aspect is a composition which comprises 5-oxo-2-pyrrolidinepropanoic acid amide in combination with a pharmaceutically acceptable carrier.

The invention sought to be patented in its pharmaceutical method aspect is a method for treating senility or for reversing amnesia, which method comprises administering an effective amount of the above defined pharmaceutical compositions to a mammal in need thereof.

DESCRIPTION OF THE PREFERRED EMBODIMENTS

The esters, salts, and amides of the invention may be readily prepared from 5-oxo-2-pyrrolidinepropanoic acid by standard methods. The synthesis of this acid is reported in Coll. Czech. Chem. Comm., 12, 278 (1947). Thus, the acid may be converted to additional compounds having structural formula I, i.e., salts, esters and amides, by standard procedures. For example, the salts may be prepared by treating the acid with an equivalent amount of a suitable base. The esters and amides may be prepared by first converting the acid to an acid halide such as the acid chloride with, for example, thionyl chloride. The so produced acid chloride may then be treated with the desired alcohol or amine, preferably in the presence of a suitable acid acceptor such as triethylamine or pyridine.

The compounds of the invention may also be prepared in an alternate preferred method, which comprises treating the compound having structural formula III with at least an approximate equal molar amount of an alcohol or amine to produce respectively an ester or amide.

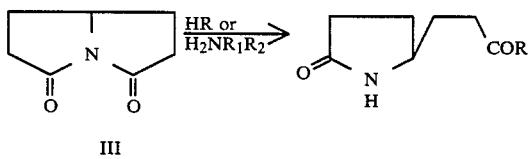

III

The synthesis of esters is conducted preferably in the presence of an acid catalyst such as a trace of hydrogen chloride, hydrogen bromide, or other strong acid. The reactants may be present in equimolar amounts although the use of water or desired alcohol in excess as the solvent is preferred.

The amides are directly prepared with an equimolar amount of the desired amine in a relatively inert or slower reacting solvent such as an alcohol or acetonitrile.

The reaction is carried out at a temperature of 25° C. to 100° C. for periods of from one to 96 hours, preferably at the boiling point of the solvent or to 150° C. Sufficient time should be allowed to effect complete reaction of starting material III for easier purification.

The product may be isolated by crystallization, chromatography or as a base addition salt by suitable adjustment of pH in the case of the free acid.

The necessary starting material, III, is a known compound synthesized in the following references: J. Amer. Chem. Soc., 69, 690–692 (1947); Coll. Czech. Chem. Comm., 12, 278–291 (1947); and Chem. Ber., 88, 509–510 (1955).

The pharmaceutically-acceptable salts of the acid are prepared by for example, suspending the acid in water and adjusting the pH with the pharmaceutically-acceptable base, or by reacting the compound of formula III with one equivalent of the pharmaceutically acceptable base in a solvent and removing the solvent under reduced pressure.

Pharmaceutically acceptable bases are organic and inorganic bases. Examples of suitable inorganic bases for salt formation are sodium hydroxide, potassium hydroxide, sodium carbonate, calcium carbonate, potassium carbonate, sodium bicarbonate, and the like.

The term pharmaceutically acceptable amine cation contemplates the positively charged ammonium ion and analogous ions derived from organic nitrogenous bases strong enough to form such cations. Bases useful for the purpose of forming pharmacologically-acceptable non-toxic addition salts of such compounds containing free carboxyl groups form a class whose limits are readily understood by those skilled in the art. Merely for illustration, they can be said to comprise, in cationic form, those of the formula:

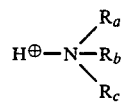

wherein $R_a$, $R_b$, and $R_c$, independently, are hydrogen, alkyl of from about one to about six carbon atoms, cycloalkyl of from about three to about six carbon atoms, aryl of about six carbon atoms, aralkyl of from about 7 to about 11 carbon atoms, hydroxyalkyl of from about two to about four carbon atoms, or monoarylhydroxyalkyl of from about 8 to about 15 carbon atoms, or, when taken together with the nitrogen atom to which they are attached, any two of $R_a$, $R_b$, and $R_c$ may form part of a 5 to 6-membered heterocyclic ring containing carbon, hydrogen, oxygen, or nitrogen, said heterocyclic rings and said aryl groups being unsubstituted or mono- or dialkyl substituted said alkyl groups containing from about one to about six carbon atoms. Illustrative therefore of $R_a$, $R_b$, and $R_c$ groups comprising pharmacologically-acceptable cations derived from ammonia or a basic amine are ammonium, mono-, di-, and trimethylammonium, mono-, di- and triethylammonium, mono-, di-, and tripropylammonium (iso and normal), ethyldimethylammonium, benzyldimethylammonium, cyclohexylammonium, benzylammonium, dibenzylammonium, piperidinium, morpholinium, pyrrolidinium, piperazinium, 1-methylpiperidinium, 4-ethylmorpholinium, 1-isopropylpyrrolidine, 1,4-dimethylpiperazinium, 1-n-butylpiperidinium, 2-methylpiperidinium, 1-ethyl-2-methylpiperidinium, mono-, di- and triethanolammonium, ethyldiethanolammonium, n-butylmonoethanolammonium, tris(hydroxymethyl)-methylammonium, phenylmonoethanolammonium, and the like.

The term, pharmaceutically acceptable metal cation contemplates the positively charged ions derived from such metals as sodium, potassium, calcium, magnesium, aluminum, zinc, iron, and the like. The salts are prepared by contacting the free form of the compound with an equivalent amount of the desired base in the conventional manner. The free forms may be regenerated by treating the salt form with an acid. For example, dilute aqueous acid solutions may be utilized to regenerate the free form from a respective salt. Dilute aqueous hydrochloric acid is suitable for this purpose. The free forms differ from their respective salt forms somewhat in certain physical properties such as solubility in polar solvents, but the salts are otherwise equivalent to their respective free base forms for purpose of the invention.

The compounds of the invention can exist in unsolvated as well as solvated forms, including hydrated forms. In general, the solvated forms, with pharmaceutically acceptable solvents such as water, ethanol, and the like are equivalent to the unsolvated forms for purposes of the invention.

The alkyl groups contemplated by the invention unless otherwise stated, comprise both straight and branched carbon chains of from one to about six carbon atoms. Representative of such groups are methyl, ethyl, isopropyl, pentyl, 3-methylpentyl, and the like.

The compounds of the invention contain an asymmetric carbon atoms which is the 2-position carbon atom of the ring marked with an asterisk. The invention contemplates the pure S isomer, the pure R isomer and mixtures thereof including the racemic mixture.

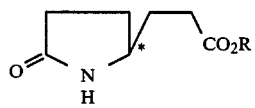

For preparing pharmaceutical compositions from the compounds described by this invention, inert, pharmaceutically acceptable carriers can be either solid or liquid. Solid form preparations include powders, tablets, dispersible granules, capsules, cachets, and suppositories. A solid carrier can be one or more substances which may also act as diluents, flavoring agents, solubilizers, lubricants, suspending agents, binders or tablet disintegrating agents; it can also be encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 or 10 to about 70 percent of the active ingredient. Suitable solid carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby to solidify.

Liquid form preparations include solutions, suspensions, and emulsions. As an example may be mentioned water or water propylene glycol solutions for parenteral injection. Liquid preparations can also be formulated in solution in aqueous polyethylene glycol solution. Aqueous solutions suitable for oral use can be prepared by dissolving the active component in water and adding suitable colorants, flavors, stabilizing and thickening agents as desired. Aqueous suspensions suitable for oral use can be made by dispersing the finely divided active component in water with viscous material, i.e., natural or synthetic gums, resins, methylcellulose, sodium carboxymethylcellulose, and other well-known suspending agents.

Also included are solid form preparations which are intended to be converted, shortly before use, to liquid form preparations for either oral or parenteral administration. Such liquid forms include solutions, suspensions, and emulsions. These particular solid form preparations are most conveniently provided in unit dose form and as such are used to provide a single liquid dosage unit. Alternately, sufficient solid may be provided so that after conversion to liquid form, multiple individual liquid doses may be obtained by measuring predetermined volumes of the liquid form preparation as with a syringe, teaspoon, or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain, in addition to the active material, flavorants, colorants, stabilizers, buffers, artificial and natural sweeteners, dispersants, thickeners, solubilizing agents, and the like. The liquid utilized for preparing the liquid form preparation may be water, isotonic water, ethanol, glycerine, propylene glycol, and the like as well as mixtures thereof. Naturally, the liquid utilized will be chosen with regard to the route of administration, for example, liquid preparations containing large amounts of ethanol are not suitable for parenteral use.

Preferably, the pharmaceutical preparation is in unit dosage form. In such form, the preparation is subdivided into unit doses containing appropriate quantities of the active component. The unit dosage form can be a packaged preparation, the package containing discrete quantities or preparation, for example, packeted tablets, capsules, and powders in vials or ampoules. The unit dosage form can also be a capsule, cachet, or tablet itself or it can be the appropriate number of any of these in packaged form.

The quantity of active compound in a unit dose of preparation may be varied or adjusted from 1 mg to 500 mg preferably to 5 to 100 mg according to the particular application and the potency of the active ingredient. The compositions can, if desired, also contain other compatible therapeutic agents.

In therapeutic use as cognition activators, the mammalian dosage range for a 70 kg subject is from 1 to 1500 mg/kg of body weight per day or preferably 25 to 750 mg/kg of body weight per day. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter the dosage is increased by small increments until the optimum effect under the circumstances is reached. For convenience, the total daily dosage may be divided and administered in portions during the day if desired.

The effectiveness of the aforementioned compounds was determined by the test designed to show the compound's ability to reverse amnesia produced by electroconvulsive shock. The test is fully described in U.S. Pat. No. 4,145,347, issued Mar. 20, 1979, and is herein incorporated by reference. The test compounds in the present instance were administered orally and the length of the electroconvulsive shock being 1.0 second.

The following criteria are used in interpreting the percent of amnesia reversal scores: 40 percent or more (active=A) 25 to 39 percent (borderline=C) and 0 to 24 percent (inactive=N).

Table 1 below reports the percent of amnesia reversal of orally administered 5-oxo-2-pyrrolidinepropanoic acid.

TABLE 1

| Dose mg/kg | 0.63 | 1.25 | 2.50 | 5.00 | 20.00 | 80.00 |
|---|---|---|---|---|---|---|
| % Reversal | 58 | 83 | 91 | 89 | 100 | 67 |
| Rating | A | A | A | A | A | A |

Table 2 below reports the percent of amnesia reversal of orally administered 5-oxo-2-pyrrolidinepropanoic acid esters.

TABLE 2

$$\text{structure: 5-oxo-pyrrolidine-N(H)-CH}_2\text{CH}_2\text{CR(=O)}$$

| R Group of Esters | Dose mg/kg | | | | | |
|---|---|---|---|---|---|---|
| | 0.63 | 1.25 | 2.50 | 5.00 | 20.00 | 80.00 |
| % Reversal (Rating) | | | | | | |
| $OCH_3$ | | | | 75(A) | 100(A) | 75(A) |
| $OCH_2C_6H_5$ | 44(A) | 56(A) | 67(A) | 64(A) | 64(A) | 71(A) |
| $OCH_2C_6H_4\text{—}\underline{p}\text{-Cl}$ | | | | 25(C) | 0(N) | 42(A) |

Table 3 below reports the percent of amnesia reversal of orally administered 5-oxo-2-pyrrolidine propanoic acid amides.

TABLE 3

| $R_1$ | $R_2$ | Dose mg/kg 1.0 | 5.0 | 10.0 | 20.0 | 80.0 | 100 |
|---|---|---|---|---|---|---|---|
| H | H[a] | 64(A) | | 33(C) | | | 64(A) |
| $-\overset{CH_3}{\underset{}{CH}}-C_6H_5$ | H | 45(A) | | 54(A) | | | 22(N) |
| $-CH_2-C_6H_5$ | H | | 50(A) / 0(N) | | 8(N) / 62(A) | 58(A) / 50(A) | |
| $-C_5H_4N$ (pyridyl) | H | 100(A) / 64(A) / 64(A) | | 100(A) / 59(A) / 48(A) | | | 100(A) / 53(A) / 48(A) |
| $-CH_2CH_2N[CH(CH_3)_2]_2$ | H | 17(N) | 33(C) | | | | 17(N) | a. Also tested at 0.1, 0.01, and 0.001 mg/kg with the following results respectively: 0(N), 28(C) and 71(A).

CHEMICAL COMPOSITIONS

Example A

Preparation of 5-Oxo-2-pyrrolidinepropanoic acid

A suspension (partial solution) of 25 g of dihydro-1H-pyrrolizine-3,5(2H,6H)-dione (III) in 150 ml of deionized water is treated with 0.1 ml of concentrated hydrochloric acid. The mixture is heated to reflux (100° C.) for 80 hours. Charcoal (0.5 g) is added and the mixture is filtered through filter aid. The solution is concentrated at reduced pressure, the 5-oxo-2-pyrrolidinepropanoic acid crystallizes and is isolated by filtration. After drying in vacuo the 5-oxo-2-pyrrolidinepropanoic acid has a melting point of 125°–127° C.

Example B

Preparation of 5-oxo-2-pyrrolidinepropanoic acid benzyl ester

Twenty-eight grams of dihydro-1H-pyrrolizine-3,5 (2H,6H)-dione (III) are dissolved in 76 g of benzyl alcohol and 0.2 ml of concentrated hydrochloric acid is added. The solution is heated at 98° C. for 104 hours. The mixture is cooled and excess benzyl alcohol is distilled at 0.1 mm pressure to a maximum bath temperature of 100° C. The residual oil is dissolved in 1 l of anhydrous diethylether, 1 g of activated charcoal is added and the resulting suspension is filtered through filter aid. The filtrate is concentrated at reduced pressure and the resulting crystals are isolated by filtration. Recrystallization from cyclohexane containing 12% methylene chloride yields 5-oxo-2-pyrrolidinepropanoic acid benzyl ester with a melting point of 79°-80° C.

Example C

Preparation of 5-oxo-2-pyrrolidinepropanoic acid methyl ester

Twenty-eight grams of dihydro-1H-pyrrolizine-3,5 (2H,6H)-dione (III) are dissolved in 100 g of methyl alcohol and 0.2 ml of concentrated hydrochloric acid is added. The solution is heated at reflux for 104 hours. The mixture is cooled and excess methyl alcohol is distilled at reduced pressure. The residual oil is dissolved in 1 l of anhydrous diethylether, 1 g of activated charcoal is added and the resulting suspension is filtered through filter aid. The filtrate is concentrated at reduced pressure and the resulting crystals are isolated by filtration. Recrystallization from methanol yields 5-oxo-2-pyrrolidinepropanoic acid methyl ester with a melting point of 52°-53° C.

Example D

Preparation of 5-oxo-2-pyrrolidinepropanoic acid ethyl ester

Twenty-eight grams of dihydro-1H-pyrrolizine-3,5 (2H,6H)-dione (III) are dissolved in 100 g of ethyl alcohol and 0.2 ml of concentrated hydrochloric acid is added. The solution is heated at reflux for 104 hours. The mixture is cooled and excess ethyl alcohol is distilled at reduced pressure. The oil is dissolved in 1 l of anhydrous diethylether, 1 g of activated charcoal is added and the resulting suspension is filtered through filter aid. The filtrate is concentrated at reduced pressure and the resulting crystals are isolated by filtration. Recrystallization from carbon tetrachloride-petroleum ether yields 5-oxo-2-pyrrolidinepropanoic acid ethyl ester with a melting point of 60°-61° C.

Example E

Preparation of 5-oxo-2-pyrrolidinepropanoic acid o-chlorobenzyl ester

Five grams of dihydro-1H-pyrrolizine-3,5(2H,6H)-dione (III) are dissolved in 31 g of o-chlorobenzyl alcohol and 0.2 ml of concentrated hydrochloric acid is added. The solution is heated at 100° C. for 71 hours. The mixture is cooled and dissolved in 150 ml of anhydrous diethylether. The solution is cooled to induce crystallization and the resulting crystals are isolated by filtration. Recrystallization from toluene-diethyl ether yields 5-oxo-2-pyrrolidinepropanoic acid o-chlorobenzyl ester with a melting point of 99°-100° C.

Example F

Preparation of 5-oxo-2-pyrrolidinepropanoic acid m-chlorobenzyl ester

Two hundred and eighty eight milligrams of dihydro-1H-pyrrolizine-3,5(2H,6H)-dione (III) are dissolved in 600 mg of m-chlorobenzyl alcohol and 0.2 ml of concentrated hydrochloric acid is added. The solution is heated at 100° C. for 40 hours. The mixture is cooled and is dissolved in 50 ml of anhydrous diethylether. The filtrate is cooled to induce crystallization and the resulting crystals are isolated by filtration. Recrystallization from toluene-petroleum ether yields 5-oxo-2-pyrrolidinepropanoic acid m-chlorobenzyl ester with a melting point of 90°-91° C.

Example G

Preparation of 5-oxo-2-pyrrolidinepropanoic acid p-chlorobenzyl ester

Five grams of dihydro-1H-pyrrolizine-3,5(2H,6H)-dione (III) are dissolved in 31 g of p-chlorobenzyl alcohol and 0.2 ml of concentrated hydrochloric acid is added. The solution is heated at 100° C. for 65 hours. The mixture is cooled and chromatographed over silica gel in dichloromethane. The starting p-chlorobenzyl alcohol is eluted with dichloromethane and the product is eluted with 2.5% methanol in dichloromethane. The eluate containing the product is concentrated at reduce pressure and the residual oil solidifies upon standing. The solid is recrystallized from toluene diethyl ether to yield 5-oxo-2-pyrrolidinepropanoic acid p-chlorobenzyl ester with a melting point of 63°-64° C.

Example H

Preparation of 5-oxo-2-pyrrolidinepropanoic acid p-trifluoromethylbenzyl ester

Five grams of dihydro-1H-pyrrolizine-3,5(2H,6H)-dione (III) are dissolved in 29 g of benzyl alcohol and 0.2 ml of concentrated hydrochloric acid is added. The solution is heated at 100° C. for 72 hours. The mixture is cooled and chromatographed over silica gel in dichloromethane. The starting p-trifluoromethylbenzyl alcohol is eluted with dichloromethane and the product is eluted with 1.0% methanol in dichloromethane. The eluate containing the product is concentrated at reduced pressure and the residual oil solidifies upon standing. The solid is recrystallized from toluenediethyl ether to yield 5-oxo-2-pyrrolidinepropanoic acid p-trifluoromethylbenzyl ester with a melting point of 81°-82° C.

Example I

Preparation of 5-oxo-2-pyrrolidinepropanoic acid p-methylbenzyl ester

Five grams of dihydro-1H-pyrrolizine-3,5(2H,6H)-dione (III) are dissolved in 27 g of p-methylbenzyl alcohol and 0.2 ml of concentrated hydrochloric acid is added. The solution is heated at 100° C. for 48. hours. The mixture is cooled and chromatographed over silica gel in dichloromethane. The starting p-methylbenzyl alcohol is eluted with dichloromethane and the product is eluted with 1.0% methanol in dichloromethane. The eluate containing the product is concentrated at reduced pressure and the residual oil solidifies upon standing. The solid is recrystallized from toluene-diethyl ether to yield 5-oxo-2-pyrrolidinepropanoic acid p-methylbenzyl ester with a melting point of 71°-72° C.

Example J

Preparation of 5-oxo-2-pyrrolidinepropanoic acid amide

A solution of 7.0 g (0.5 mol) of dihydro-1H-3,5-(2H,6H)dioxopyrrolizidine in 100 ml of ethanol is saturated with anhydrous ammonia and is allowed to stand for 48 hours. The solution is evaporated and the residue after two recrystallizations from n-butanol yields 5-oxo- 2-pyrrolidinepropanoic acid amide with a melting point of 177.5°–178° C.

Example K

Preparation of 5-oxo-2-pyrrolidinepropanoic acid N-benzyl amide

A solution of 7.0 g (0.05 mol) of dihydro-1H-3,5-(2H,6H)dioxopyrrolizidine in 50 ml of ethanol is treated with 5.4 g (0.5 mol) of benzyl amine. The mixture is refluxed for 48 hours and is concentrated at reduced pressure.

The residue is chromatographed over silica gel in chloroform, followed by elution with 5% methanol in chloroform. After concentration at reduced pressure, 5-oxo-2-pyrrolidinepropanoic acid N-benzyl amide has a melting point of 140°–142° C.

Example L

Preparation of 5-oxo-2-pyrrolidinepropanoic acid N-N',N'-diisopropylaminoethyl Amide A solution of 7.0 g (0.05 mol) of dihydro-1H-3,5-(2H,6H)dioxopyrrolizidine in 50 ml of ethanol is treated with 7.2 g (0.05 mol) of N-N',N'-diisopropylaminoethylamine.

The mixture is refluxed for 24 hours and is concentrated at reduced pressure. The residue is chromatographed over silica gel in methanol and concentrated at reduced pressure. The residue is dissolved in anhydrous diethyl ether, charcoaled and cooled to dry ice temperatures. The crystals of 5-oxo-2-pyrrolidinepropanoic acid N-N',N'-diisopropylaminoethyl amide are isolated by filtration and after drying in a vacuum oven have a melting point of 62°–65° C.

Example M

Preparation of 5-oxo-2-pyrrolidinepropanoic acid N-(L)alpha-methylbenzyl amide

A mixture of 7.0 g (0.05 mol) of dihydro-1H-3,5-(2H,6H)dioxopyrrolizidine and 8.4 g (0.07 mol) L-alpha-methylbenzylamine is heated at 110° C. for 16 hours and at 160° C. for 24 hours. The residue is heated at reduced pressure and upon cooling melts at 100°–107° C. Chromatography of the residue over silica gel and elution with 5% methanol in methylene chloride yields 5-oxo-2-pyrrolidinepropanoic acid N-(L)-alpha-methylbenzyl amide with a melting point of 108°–112° C.

Example N

Preparation of 5-oxo-2-pyrrolidinepropanoic acid N-(4-pyridinyl) amide

A mixture of 1.5 g (0.0108 mol) of dihydro-1H-3,5-(2H,6H)dioxopyrrolizidine and 1.14 g (0.012 mol) of 4-aminopyridine is heated at 150° C. for 24 hours. The residue has a melting point of 180°–184° C. The residue is chromatographed over silica gel using 10% methanol in methylene chloride for elution. After recrystallization from acetonitrile the crystalline 5-oxo-2-pyrrolidinepropanoic acid N-(4-pyridinyl) amide has a melting point of 187°–188° C.

Example O

Preparation of 5-oxo-2-pyrrolidine-propanoic acid N-(2,6-dimethylphenyl) amide

A mixture of 7.0 g (0.05 mol) of dihydro-1H-3,5-(2H,6H)dioxopyrrolizidine and 13.3 g (0.11 mol) of 2,6-dimethylaniline is heated at 140° C., for 72 hours. The residue is crushed and extracted with boiling dichloromethane. The residue is recrystallized from a 1:1 mixture of isopropanol and methanol to yield 5-oxo-2-pyrrolidinepropanoic acid N-(2,6-dimethylphenyl) amide with a melting point of 206°–208° C.

Example P

Preparation of 5-oxo-2-pyrrolidinepropanoic acid N-4-(3-nitro-1-oxide-pyridinyl) Amide A mixture of 7.0 g (0.05 mol) of dihydro-1H-3,5-(2H,6H)dioxopyrrolizidine and 7.3 g (0.05 mol) of 4-amino-3-nitro-pyridine-1-oxide (Synthesized as in Chem. Pharm. Bull. (Tokyo) 12, 866–872 (1964), Chem. Abstr., 61, 14661a (1964)) is heated at 160° C. for 18 hours, and the residue is recrystallized from acetonitrile to afford crystalline 5-oxo-2-pyrrolidinepropanoic acid N-4-(3-nitro-1-oxide-pyridinyl) amide.

Example Q

Preparation of 5-oxo-2-pyrrolidinepropanoic acid 4-(3-aminopyridinyl) amide

A solution of 14.3 g (0.05 mol) of 5-oxo-2-pyrrolidinepropanoic acid N-4-(3-nitro-1-oxidepyridinyl) amide in 200 ml of ethanol is treated with hydrogen in the presence of Raney Nickel catalyst. The mixture is filtered and concentrated to yield 5-oxo-2-pyrrolidinepropanoic acid 4-(3-aminopyridinyl) amide.

Example R

Preparation of 5-oxo-2-pyrrolidinepropanoic acid N-3-(4-nitro-1-oxide-pyridinyl) amide A mixture of 7.0 g (0.05 mol) of dihydro-1H-3,5-(2H,6H)dioxopyrrolizidine and 7.3 g (0.05 mol) of 3-amino-4-nitro-pyridine-1-oxide (Synthesized as in Roczniki Chem., 38, 777–784 (1964), Chem Abstr., 61, 10653c (1964)) is heated at 160° C. for 18 hours. The residue is recrystallized from acetonitrile to afford crystalline 5-oxo-2-pyrrolidinepropanoic acid N-3-(4-nitro-1-oxide-pyridinyl) amide.

Example S

Preparation of 5-oxo-2-pyrrolidinepropanoic acid 3-(4-aminopyridinyl) amide

A solution of 14.3 g (0.05 mol) of 5-oxo-pyrrolidin-2-propanoic acid N-3-(4-nitro-1-oxidepyridinyl) amide in 200 ml of ethanol is treated with hydrogen in the presence of Raney Nickel catalyst. The mixture is filtered and concentrated to yield 5-oxo-2-pyrrolidinepropanoic acid 3-(4-aminopyridinyl) amide.

The invention is further illustrated by the following Examples of tablets containing 1.0, 2.5, 25, 50 mg; capsules containing 1.0, 2.5, 25, 50 mg respectively of active ingredient, an example of a parenteral formulation, an example of a Rectal Suppository formulation, an example of a Suspension formulation and an example of a Syrup for Reconstitution.

PHARMACEUTICAL COMPOSITIONS

Example 1

| Ingredient | Quantity |
| --- | --- |
| 5-Oxo-2-pyrrolidinepropanoic acid | 150 g |
| Lactose | 1124 g |
| Corn Starch | 39 g |
| Hydroxypropyl cellulose | 30 g |
| Magnesium stearate | 7 g |

-continued

| Ingredient | Quantity |
|---|---|
| Ethanol-water 50:50 | qs |

The 5-oxo-2-pyrrolidinepropanoic acid, lactose, and hydroxypropyl cellulose are blended and granulated with 50:50 ethanol-water. The wet granulation is screened, dried, and rescreened. The resulting dried granulation is blended with magnesium stearate and the corn starch and the mixture is compressed into 225 mg tablets using an 11/32 inch standard concave punch. Yield equals approximately 6000 tablets each containing 25.0 mg of 5-oxo-2-pyrrolidinepropanoic acid.

Example 2

| Ingredient | Quantity |
|---|---|
| 5-Oxo-2-pyrrolidinepropanoic acid | 15 g |
| Lactose | 1249 g |
| Corn Starch | 39 g |
| Hydroxypropyl cellulose | 30 g |
| Magnesium stearate | 7 g |
| Ethanol-water 50:50 | qs |

The 5-oxo-2-pyrrolidinepropanoic acid, lactose, and hydroxypropyl cellulose are blended and granulated with 50:50 ethanol-water. The wet granulation is screened, dried, and rescreened. The resulting dried granulation is blended with magnesium stearate and the corn starch and the mixture is compressed into 225 mg tablets using an 11/32 inch standard concave punch. Yield equals approximately 6000 tablets each containing 2.5 mg of 5-oxo-2-pyrrolidinepropanoic acid.

Example 3

| Ingredient | Quantity |
|---|---|
| 5-Oxo-2-pyrrolidinepropanoic acid | 6 g |
| Lactose | 1268 g |
| Corn Starch | 39 g |
| Hydroxypropyl cellulose | 30 g |
| Magnesium stearate | 7 g |
| Ethanol-water 50:50 | qs |

The 5-oxo-2-pyrrolidinepropanoic acid, lactose, and hydroxypropyl cellulose are blended and granulated with 50:50 ethanol-water. The wet granulation is screened, dried, and rescreened. The resulting dried granulation is blended with magnesium stearate and the corn starch and the mixture is compressed into 225 mg tablets using an 11/32 inch standard concave punch. Yield equals approximately 6000 tablets each containing 1.0 mg of 5-oxo-2-pyrrolidinepropanoic acid.

Example 4

| Ingredient | Quantity |
|---|---|
| 5-Oxo-2-pyrrolidinepropanoic acid | 300 g |
| Lactose | 974 g |
| Corn Starch | 39 g |
| Hydroxypropyl cellulose | 30 g |
| Magnesium stearate | 7 g |
| Ethanol-water 50:50 | qs |

The 5-oxo-2-pyrrolidinepropanoic acid, lactose, and hydroxypropyl cellulose are blended and granulated with 50:50 ethanol-water. The wet granulation is screened, dried, and rescreened. The resulting dried granulation is blended with magnesium stearate and the corn starch and the mixture is compressed into 225 mg tablets using an 11/32 inch standard concave punch. Yield equals approximately 6000 tablets each containing 50.0 mg of 5-oxo-2-pyrrolidinepropanoic acid.

Example 5

| Ingredient | Quantity |
|---|---|
| 5-Oxo-2-pyrrolidinepropanoic acid | 250 g |
| Lactose | 1723 g |
| Magnesium stearate | 27 g |

The mixture is blended and filled into No. 4 hard gelatin capsules, filling each capsule with 200 mg of the powder mixture. Yield equals approximately 10,000 capsules each containing 25.0 mg of 5-oxo-2-pyrrolidinepropanoic acid.

Example 6

| Ingredient | Quantity |
|---|---|
| 5-Oxo-2-pyrrolidinepropanoic acid | 25 g |
| Lactose | 1948 g |
| Magnesium stearate | 27 g |

The mixture is blended and filled into No. 4 hard gelatin capsules, filling each capsule with 200 mg of the powder mixture. Yield equals approximately 10,000 capsules each containing 2.5 mg of 5-oxo-2-pyrrolidinepropanoic acid.

Example 7

| Ingredient | Quantity |
|---|---|
| 5-Oxo-2-pyrrolidinepropanoic acid | 10 g |
| Lactose | 1963 g |
| Magnesium stearate | 27 g |

The mixture is blended and filled into No. 4 hard gelatin capsules, filling each capsule with 200 mg of the powder mixture. Yield equals approximately 10,000 capsules each containing 1.0 mg of 5-oxo-2-pyrrolidinepropanoic acid.

Example 8

| Ingredient | Quantity |
|---|---|
| 5-Oxo-2-pyrrolidinepropanoic acid | 500 g |
| Lactose | 1473 g |
| Magnesium stearate | 27 g |

The mixture is blended and filled into No. 4 hard gelatin capsules, filling each capsule with 200 mg of the powder mixture. Yield equals approximately 10,000 capsules each containing 50.0 mg of 5-oxo-2-pyrrolidinepropanoic acid.

The invention is further illustrated by the following example of a 2 gram rectal suppository. The suppository can contain a range of from 30 mg to 500 mg of active ingredient.

Example 9

| Ingredient | Quantity |
|---|---|
| 5-Oxo-2-pyrrolidinepropanoic acid | 30 mg |
| Witepsol H35 | 1.97 g |

The Witepsol H35 is melted by heating to 38° C., 5-oxo-2-pyrrolidinepropanoic acid is added and mixed until thoroughly dispersed and placed in a mold at 33°–34° C.

The invention is further illustrated by the following example of a suspension formulation. The suspension can contain a range of active ingredient from 50 mg/5 ml to 1 g/5 ml.

Example 10

| Ingredient | Quantity |
|---|---|
| 5-Oxo-2-pyrrolidinepropanoic acid | 10 g |
| Saccharin Sodium | 0.5 g |
| Thihydroxysterain | 0.75 g |
| Propylparaben | 0.1 g |
| Imitation Cherry Flavor | 2 ml |
| Neobee M-5 q.s. ad | 100 ml |

Propylparaben is dissolved in a portion of the Neobee M-5, the trihydroxystearin is added and the mixture is homogenized for 30 minutes while maintaining the temperature between 50°–60° C. The mixture is cooled and the 5-oxo-2-pyrrolidinepropanoic acid, saccharin sodium and imitation cherry flavor are added. The volume is made up with Neobee M-5.

The invention is further illustrated by the following example of Syrup for Reconstitution. The syrup can contain between 50 mg/5 ml and 500 mg/15 ml.

Example 11

| Ingredient | Quantity |
|---|---|
| 5-Oxo-2-pyrrolidinepropanoic acid | 10 g |
| Sugar granulated, Bottlers grade | 60 g |
| Artificial Peppermint Flavor, Water soluble (American Flavor and Fragrance) | 0.4 g |
| Water q.s. ad | 100 ml |

The 5-oxo-2-pyrrolidinepropanoic acid, granulated sugar, and artificial peppermint flavor are dry blended. The blend is filled into 4 oz bottle with a 100 ml calibration mark. At time of dispensing make up to volume with water and shake until all solids are dissolved. The mixture is refrigerated and used within 7 days.

The invention is further illustrated by the following Examples of tablets containing 1.0, 2.5, 25, 50 mg; capsules containing 1.0, 2.5, 25, 50 mg respectively of active ingredient, an example of a parenteral formulation, an example of a Rectal Suppository formulation, a Suspension formulation, and a Syrup for Reconstitution formulation.

Example 12

| Ingredient | Quantity |
|---|---|
| 5-Oxo-2-pyrrolidinepropanoic acid benzyl ester | 150 g |
| Lactose | 1124 g |
| Corn Starch | 39 g |
| Hydroxypropyl cellulose | 30 g |
| Magnesium stearate | 7 g |
| Ethanol-water 50:50 | qs |

The 5-oxo-2-pyrrolidinepropanoic acid benzyl ester, lactose, and hydroxypropyl cellulose are blended and granulated with 50:50 ethanol-water. The wet granulation is screened, dried, and rescreened. The resulting dried granulation is blended with magnesium stearate and the corn starch and the mixture is compressed into 225 mg tablets using an 11/32 inch standard concave punch. Yield equals approximately 6000 tablets each containing 25.0 mg of 5-oxo-2-pyrrolidinepropanoic acid benzyl ester.

Example 13

| Ingredient | Quantity |
|---|---|
| 5-Oxo-2-pyrrolidinepropanoic acid benzyl ester | 15 g |
| Lactose | 1249 g |
| Corn Starch | 39 g |
| Hydroxypropyl cellulose | 30 g |
| Magnesium stearate | 7 g |
| Ethanol-water 50:50 | qs |

The 5-oxo-2-pyrrolidinepropanoic acid benzyl ester, lactose, and hydroxypropyl cellulose are blended and granulated with 50:50 ethanol-water. The wet granulation is screened, dried, and rescreened. The resulting dried granulation is blended with magnesium stearate and the corn starch and the mixture is compressed into 225 mg tablets using an 11/32 inch standard concave punch. Yield equals approximately 6000 tablets each containing 2.5 mg of 5-oxo-2-pyrrolidinepropanoic acid benzyl ester.

Example 14

| Ingredient | Quantity |
|---|---|
| 5-Oxo-2-pyrrolidinepropanoic acid benzyl ester | 6 g |
| Lactose | 1268 g |
| Corn Starch | 39 g |
| Hydroxypropyl cellulose | 30 g |
| Magnesium stearate | 7 g |
| Ethanol-water 50:50 | qs |

The 5-oxo-2-pyrrolidinepropanoic acid benzyl ester, lactose, and hydroxypropyl cellulose are blended and granulated with 50:50 ethanol-water. The wet granulation is screened, dried, and rescreened. The resulting dried granulation is blended with magnesium stearate and the corn starch and the mixture is compressed into 225 mg tablets using an 11/32 inch standard concave punch. Yield equals approximately 6000 tablets each containing 1.0 mg of 5-oxo-2-pyrrolidinepropanoic acid benzyl ester.

Example 15

| Ingredient | Quantity |
|---|---|
| 5-Oxo-2-pyrrolidinepropanoic acid benzyl ester | 300 g |
| Lactose | 974 g |
| Corn Starch | 39 g |

-continued

| Ingredient | Quantity |
| --- | --- |
| Hydroxypropyl cellulose | 30 g |
| Magnesium stearate | 7 g |
| Ethanol-water 50:50 | qs |

The 5-oxo-2-pyrrolidinepropanoic acid benzyl ester, lactose, and hydroxypropyl cellulose are blended and granulated with 50:50 ethanol-water. The wet granulation is screened, dried, and rescreened. The resulting dried granulation is blended with magnesium stearate and the corn starch and the mixture is compressed into 225 mg tablets using an 11/32 inch standard concave punch. Yield equals approximately 6000 tablets each containing 50.0 mg of 5-oxo-2-pyrrolidinepropanoic acid benzyl ester.

Example 16

| Ingredient | Quantity |
| --- | --- |
| 5-Oxo-2-pyrrolidinepropanoic acid benzyl ester | 250 g |
| Lactose | 1723 g |
| Magnesium stearate | 27 g |

The mixture is blended and filled into No. 4 hard gelatin capsules, filling each capsule with 200 mg of the powder mixture. Yield equals approximately 10,000 capsules each containing 25.0 mg of 5-oxo-2-pyrrolidinepropanoic acid benzyl ester.

Example 17

| Ingredient | Quantity |
| --- | --- |
| 5-Oxo-2-pyrrolidinepropanoic acid benzyl ester | 25 g |
| Lactose | 1948 g |
| Magnesium stearate | 27 g |

The mixture is blended and filled into No. 4 hard gelatin capsules, filling each capsule with 200 mg of the powder mixture. Yield equals approximately 10,000 capsules each containing 2.5 mg of 5-oxo-2-pyrrolidinepropanoic acid benzyl ester.

Example 18

| Ingredient | Quantity |
| --- | --- |
| 5-Oxo-2-pyrrolidinepropanoic acid benzyl ester | 500 g |
| Lactose | 1473 g |
| Magnesium stearate | 27 g |

The mixture is blended and filled into No. 4 hard gelatin capsules, filling each capsule with 200 mg of the powder mixture. Yield equals approximately 10,000 capsules each containing 50.0 mg of 5-oxo-2-pyrrolidinepropanoic acid benzyl ester.

The invention is further illustrated by the following example of a 2 gram rectal suppository. The suppository can contain a range of from 30 mg to 500 mg of active ingredient.

Example 19

| Ingredient | Quantity |
| --- | --- |
| 5-Oxo-2-pyrrolidinepropanoic acid benzyl ester | 30 mg |
| Witepsol H35 | 1.97 g |

The Witepsol H35 is melted by heating to 38° C., 5-oxo-2-pyrrolidinepropanoic acid benzyl ester is added and mixed until thoroughly dispersed and placed in a mold at 33°–34° C.

The invention is further illustrated by the following example of a suspension formulation. The suspension can contain a range of active ingredient from 50 mg/5 ml to 1 g/5 ml.

Example 20

| Ingredient | Quantity |
| --- | --- |
| 5-Oxo-2-pyrrolidinepropanoic acid benzyl ester | 10 g |
| Saccharin Sodium | 0.5 g |
| Trihydroxystearin | 0.75 g |
| Propylparaben | 0.1 g |
| Imitation Cherry Flavor | 2 ml |
| Neobee M-5 q.s. ad | 100 ml |

Propylparabene is dissolved in a portion of the Neobee M-5, the trihyroxystearin is added and the mixture is homogenized for 30 minutes while maintaining the temperature between 50°–60° C. The mixture is cooled and the 5-oxo-2-pyrrolidinepropanoic acid benzyl ester, saccharin sodium, and imitation cherry flavor are added. The volume is made up with Neobee M-5.

The invention is further illustrated by the following example of a Syrup for Reconstitution. The syrup can contain between 50 mg/5 ml and 500 mg/15 ml.

Example 21

| Ingredient | Quantity |
| --- | --- |
| 5-Oxo-2-pyrrolidinepropanoic acid benzyl ester | 10 g |
| Sugar granulated, Bottlers grade | 60 g |
| Artificial Peppermint Flavor, Water Soluble (American Flavor and Fragrance) | 0.4 g |
| Water q.s. ad | 100 ml |

The 5-oxo-2-pyrrolidinepropanoic acid benzyl ester, granulated sugar, and artificial peppermint flavor are dry blended. The blend is is filled into 4 oz bottle with a 100 ml calibration mark. At time of dispensing make up to volume with water and shake until all solids are dissolved. The mixture is refrigerated and used within seven days.

I claim:

1. A compound having the structural formula

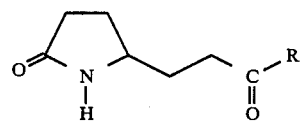

wherein R is selected from

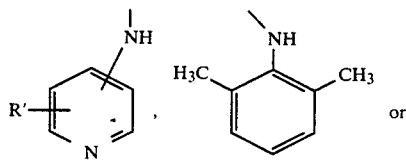, 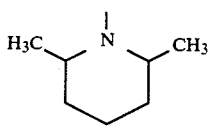 or where R' is amino, alkylamino, or dialkylamino of from one to six carbon atoms.

2. The compound defined in claim 1 having the name of 5-oxo-2-pyrrolidinepropanoic acid N-4-(pyridinyl)amide.

3. The compound defined in claim 1 having the name of 5-oxo-2-pyrrolidinepropanoic acid 4-(3-aminopyridinyl)amide.

4. The compound defined in claim 1 having the name of 5-oxo-2-pyrrolidinepropanoic acid 3-(4-aminopyridinyl)amide.

5. A pharmaceutical composition comprising an electroconvulsive shock-induced amnesia reversing effective amount of a compound as defined by claim 1 in combination with a pharmaceutically acceptable carrier.

6. A method for reversing amnesia caused by electroconvulsive shock in a mammal in need of said treatment, which method comprises administering to said mammal the pharmaceutical composition defined in claim 5.

* * * * *